(12) United States Patent
Zilbershtein et al.

(10) Patent No.: US 8,921,251 B2
(45) Date of Patent: Dec. 30, 2014

(54) CATALYST SYSTEM AND PROCESSES FOR THE (CO-) TRIMERIZATION OF OLEFINS AND THE (CO-) POLYMERIZATION OF OLEFIN OLIGOMERS

(75) Inventors: Timur Mikhailovich Zilbershtein, Kazan (RU); Maxim Vladimirovich Lipskikh, Tomsk (RU); Alexei Alexandrovich Nosikov, Tomskaya (RU); Georgy Viktorovich Nesyn, Tomsk (RU)

(73) Assignee: Open Joint Stock Company "Sibur Holding", Moscow (RU)

( * ) Notice: Subject to any disclaimer, the term of this patent is extended or adjusted under 35 U.S.C. 154(b) by 0 days.

(21) Appl. No.: 13/575,902

(22) PCT Filed: Jan. 28, 2011

(86) PCT No.: PCT/RU2011/000049
§ 371 (c)(1),
(2), (4) Date: Jul. 27, 2012

(87) PCT Pub. No.: WO2011/093748
PCT Pub. Date: Aug. 4, 2011

(65) Prior Publication Data
US 2012/0302715 A1    Nov. 29, 2012

(30) Foreign Application Priority Data

Jan. 29, 2010 (RU) ................................ 2010103074

(51) Int. Cl.
| B01J 37/34 | (2006.01) |
| B01J 23/00 | (2006.01) |
| C08F 4/24 | (2006.01) |
| C08F 4/44 | (2006.01) |
| C08F 4/52 | (2006.01) |
| C07C 2/24 | (2006.01) |
| B01J 31/18 | (2006.01) |
| B01J 31/14 | (2006.01) |
| C07C 2/32 | (2006.01) |
| C08F 110/02 | (2006.01) |

(52) U.S. Cl.
CPC ............ B01J 31/181 (2013.01); *B01J 2531/62* (2013.01); *C08F 110/02* (2013.01); *C07C 2531/14* (2013.01); *C07C 2531/22* (2013.01); *B01J 2231/12* (2013.01); B01J 31/143 (2013.01); *B01J 2231/20* (2013.01); C07C 2/32 (2013.01)
USPC ............... 502/5; 502/319; 526/106; 526/141; 526/522; 585/513; 585/522

(58) Field of Classification Search
USPC .............. 502/256, 319, 5; 526/106, 141, 185; 585/513, 522
See application file for complete search history.

(56) References Cited

U.S. PATENT DOCUMENTS

| 3,962,182 | A | 6/1976 | Steele et al. |
| 5,719,095 | A | 2/1998 | Brekner et al. |
| 5,786,431 | A * | 7/1998 | Reagen et al. ................. 526/113 |
| 6,455,648 | B1 | 9/2002 | Freeman et al. |
| 6,800,702 | B2 | 10/2004 | Wass |
| 7,384,886 | B2 | 6/2008 | Knudsen et al. |
| 2009/0233005 | A1 * | 9/2009 | Everaert ........................ 427/553 |

FOREIGN PATENT DOCUMENTS

| DE | 10200740 A1 | 8/2003 | |
| EP | 608447 A1 * | 8/1994 | ............... C08F 10/00 |
| EP | 2098543 A1 * | 9/2009 | ............... C07C 2/24 |
| GB | 1530445 A | 11/1978 | |
| JP | H10-007595 A | 1/1998 | |
| JP | 2000-176291 A | 6/2000 | |
| JP | 2008-007697 A | 1/2008 | |
| JP | 2008-052724 A | 3/2008 | |
| JP | 2008-540758 A | 11/2008 | |
| RU | 2104088 C1 | 2/1998 | |
| RU | 2169167 C1 | 6/2001 | |

OTHER PUBLICATIONS

International Search Report, International Application No. PCT/RU2011000049, Date of Completion of Search May 11, 2011, 1 page.
Yang, Y. et al, "Roles of Chloro Compound in Homogeneous [Cr92-ethyhexanoate)3/2,5-dimethylpyrrole/triethylaluminum/chloro compound] Catalyst System for Ethylene Trimerization", Applied Catalysis, vol. 193, 2000, pp. 29-38, 10 pages.
International Preliminary Report on Patentability (English version), International Application No. PCT/RU2011000049, date of completion of the report Apr. 10, 2012, 5 pages.
European Search Report for PCT/RU2011000049 date Jun. 13, 2013 (6 pages).

* cited by examiner

*Primary Examiner* — David W Wu
*Assistant Examiner* — Elizabeth Eng
(74) *Attorney, Agent, or Firm* — Fitch Even Tabin & Flannery LLP

(57) ABSTRACT

The invention relates to the field of producing polymers and copolymers of olefin oligomers produced by a trimerization reaction of olefin monomers. There is disclosed a process which comprises producing olefin oligomers with the aid of a trimerization catalyst system prepared using UHF irradiation for activating individual components of the trimerization catalyst system. The use of the trimerization catalyst system thus improved and having increased activity provides for increased effectiveness in the production of olefin oligomers from ethylene or other olefin monomers, inter alia, at a low pressure of ethylene. The olefin oligomers thus produced are then polymerized or copolymerized using processes known in the art.
The technical effect consists in increasing the effectiveness of the production of olefin oligomers which are then used in a polymerization or copolymerization reaction.

28 Claims, No Drawings

CATALYST SYSTEM AND PROCESSES FOR THE (CO-) TRIMERIZATION OF OLEFINS AND THE (CO-) POLYMERIZATION OF OLEFIN OLIGOMERS

FIELD OF THE INVENTION

The invention relates to the field of polymerization and copolymerization of olefins to produce valuable polymer products, such as low density linear polyethylene, polyhexene and the like, based on a light olefin monomer, for example ethylene. For this purpose, such olefin monomer is subjected to the trimerization reaction to produce olefin oligomer for subsequent polymerization or copolymerization thereof. Therefore, the present invention relates to preparation of a catalyst or a cocatalyst used in the process of trimerization and/or oligomerization of olefins, and to the processes of trimerization and/or oligomerization of olefins themselves.

BACKGROUND

U.S. Pat. No. 6,455,648 discloses an olefin oligomerization catalyst system comprising: a chromium source, a pyrrole-containing compound, a metal alkyl, and a halide source, and a process for preparing thereof, implemented in four embodiments differing by the order of mixing the components of said system in an inert atmosphere. U.S. Pat. No. 6,455,648 also discloses a process for oligomerization of olefins by using said chromium-based catalyst system, wherein ethylene is fed at pressure of about 51 bar and temperature of 110° C. The use of the above catalyst system in the ethylene oligomerization process allows obtaining selectivity with respect to a target product of the trimerization process, hexene-1, up to 96.4%, and the selectivity with respect to hexene-1 in the hexene fraction up to 99.6%. The catalytic activity of the system is 73,400 g/(g Cr·hr) calculated on the basis of the liquid reaction products. Disadvantage of such catalyst system is formation of by-products, including decenes, in the oligomerization process, which leads to reducing the target product selectivity, and necessity of using high temperature and pressure.

U.S. Pat. No. 6,800,702 discloses the possibility of trimerization of olefins by using a highly active catalyst system formed by the chromium salt $CrCl_3(THF)_3$, a diphosphazane ligand of formula $R_2PN(Alk)PR_2$, wherein R is 2-methoxyphenyl and Alk is methyl or another alkyl, and methylalumoxane (MAO), in a Cr:ligand:MAO ratio of 1:1:300. It allows the ethylene trimerization reaction at low pressure of ethylene and simultaneous or subsequent polymerization or copolymerization of the olefin oligomer formed. The activity of the trimerization catalyst system reaches 175,300 g/(g Cr·hr) at a pressure of 8 bar. Disadvantage of said method consists in that considerable excess of the expensive MAO reagent is used for preparing said catalyst system, as well as expensive diphosphazane compounds as the components of the trimerization catalyst system. Thus, when re-calculating the outcome obtained at a pressure of 20 bar on the basis of the amount of aluminum used, the activity of the catalyst system at the pressure of 8 bar is 1,125 g/(g Al·hr).

The closest prior art for the present invention is a process of trimerization and oligomerization of olefin monomers to produce an olefin oligomer, which then can be polymerized and/or copolymerized, disclosed in patent RU 2104088. The catalyst system according to this invention consists of: a chromium salt, such as chromium (III) ethylhexanoate; a pyrrolic compound, for example 2,5-dimethylpirrole; alkyl metal, preferably, alkylaluminium, for example triethylaluminium (TEA); and, optionally, a halide source, halogen-containing compound, for example $GeCl_4$ or $AlEt_2Cl$. The properties of said catalyst systems are defined, firstly, by their composition and a ratio of initial components, including a solvent; secondly, by the method of mixing the initial components. The patent also discloses the possibility of an olefin trimerization process with subsequent or simultaneous copolymerization of the resultant olefin oligomer and an olefin compound. The maximum catalyst activity, according to the examples provided in the patent, is 66,400 g/(g Cr·hr) at ethylene pressure of 550 psi, or 37.4 bar, and temperature of 80° C. The Cr:Al ratio is 1:15. Thus, the specific activity of the catalyst system calculated on the basis of the amount of aluminum is 8,525 g/(g Al·hr). However, the ethylene trimerization process requires comparatively high pressure. Although the reaction is possible at significantly lower pressure down to atmospheric, it is more preferable to use the ethylene pressure not lower than 12 bar; otherwise, the rate of the reaction and the productivity of the catalyst system drop to a low level. As known from the article in Applied Catalysis A: General, vol. 193 (2000), pp. 29-38, the rate of the trimerization reaction for the chromium-based catalyst system is proportional to the square of ethylene pressure. Thus, in decreasing the pressure from 37.4 bar to 12 bar, the catalytic activity decreases in about 10 times, and, in decreasing the pressure to 8 bar, it decreases in 21 times, i.e., to about 400 g/(g Al·hr). The above patent discloses various embodiments of preparation of catalyst systems for trimerization, oligomerization, and polymerization processes. Disadvantages of the prototype are the necessity of using expensive germanium tetrachloride as a halide source to achieve high activity and selectivity of the system, and considerable decrease in the activity of the catalyst system when decreasing the pressure. Therefore, it is necessary to use increased pressure of ethylene, which, in turn, leads to high capital expenditures for the equipment.

SUMMARY OF THE INVENTION

The object of the present invention is to increase the selectivity of the reaction of oligomerization and trimerization of olefins and to achieve the high activity of the trimerization and oligomerization catalyst system at low pressure of ethylene. Another object of the invention is to provide a high effectiveness of the process of polymerization or copolymerization of olefins produced by trimerization or cotrimerization of olefin monomers at low pressure of the olefin monomers.

The object is solved by using UHF irradiation of an alkylaluminum component comprised in the catalyst system, when preparing the trimerization catalyst system according to the invention.

Thus, the present invention relates to a method of preparing a catalyst system for trimerization/co-trimerization and/or oligomerization/co-oligomerization of olefin monomers, comprising mixing a chromium source compound, a nitrogen-containing ligand and alkylaluminum, wherein the method is characterized in that, in preparing the trimerization catalyst system, alkylaluminum is exposed to UHF radiation.

The invention also relates to the catalyst system for trimerization/co-trimerization and/or oligomerization/co-oligomerization of an olefin monomer, prepared according to said method.

The invention also relates to the process of trimerization/co-trimerization and/or oligomerization/cooligomerization of an olefin compound comprising from 2 to 30 carbon atoms/molecule, preferably an olefin monomer comprising from 2 to 6 carbon atoms/molecule, and at least one terminal olefinic double bond, wherein the process is characterized in that it comprises a step of (co-)trimerization and/or (co-)oligomerization in the presence of said catalyst system.

The invention also relates to the process of polymerization or copolymerization of an olefin oligomer, wherein the olefin oligomer is produced by said (co-)trimerization and/or (co-)oligomerization process.

The present invention provides improved activity of the trimerization catalyst, which allows trimerization of an olefin monomer, with subsequent or simultaneous polymerization or copolymerization, at low pressure of the olefin monomer. With that, the rate of production of olefin oligomers is higher than the rate of production of olefin oligomers with using the catalyst system prepared without UHF irradiation according to the method disclosed in patent RF 2104088. Thus, in comparison with the closest prior art, the reaction can be effectively carried out at pressure lower than the pressure in case of using the trimerization catalyst system according to the closest prior art. The use of the process on an industrial scale decreases capital expenditures for the equipment.

DETAILED DESCRIPTION

The object of the present invention is solved by preparing the catalyst system according to the invention by the method comprising mixing of components that are often used for this purpose in the relevant art, in particular: 1) a chromium source; 2) a nitrogen-containing ligand; and 3) alkylaluminum, and 4) optionally, a halide source compound.

As the chromium source, an organic or inorganic chromium compound or a mixture thereof can be used. The oxidation state of chromium can vary from 0 to 6. Generally, the chromium source has formula $CrX_n$, wherein X can be the same or different organic or inorganic moieties, and n is an integer of 1 to 6. Organic moieties can have from 1 to 20 carbon atoms and are selected from the group consisting of: alkoxy, alkylcarbonyl, ketone, pyrrolide, and amide. Inorganic moieties include, for example, but are not limited to: halides, sulfates and/or oxides. Examples of chromium compounds include, for example, but are not limited to, chromium (III) chloride, chromium (III) acetate, chromium (III) trisethylhexanoate, chromium (III) acetylacetonate, chromium (III) pyrrolide, chromium (III) acetate.

An organic compound comprising a pyrrole ring moiety, in particular a 5-membered aromatic ring with one nitrogen atom, can be used as the nitrogen-containing ligand. Examples of nitrogen-containing ligands include, but are not limited to: pyrrole, 2,5-dimethylpyrrole, lithium pyrrolide ($C_4H_4NLi$), 2-ethylpyrrole, indole, 2-methylindole, 4,5,6,7-tetrahydroindole. Pyrrole or 2,5-dimethylpyrrole is most preferable.

Alkylaluminum can be an alkylaluminum compound, a halogenated alkylaluminum compound, an alcoxyaluminum compound, and mixtures thereof. The use of the compounds that have not been contacted with water, i.e. unhydrolyzed compounds, are preferable to improve selectivity. If a desired product is the trimerization catalyst system, alkylaluminum should include at least one unhydrolyzed compound of the following general formula: $AlR_3$, $AlR_2X$, $AlRX_2$, $AlR_2OR$, $AlRXOR$ and/or $Al_2R_3X_3$, wherein R is an alkyl group, X is a halogen atom. Examples of such compounds include, but are not limited to: triethylaluminum, diethylaluminum chloride, tripropylaluminum, triisobutylaluminum, diethylaluminum ethoxide and/or ethylaluminum sesquichloride. Trialkylaluminum compounds are preferable. Triethylaluminum or a mixture of triethylaluminum and diethylaluminum chloride is most preferable trialkylaluminum compounds.

In the catalyst system a halide source can be added as an additional component. The halide source can be any compound comprising a halogen atom. Examples of halides can include: fluoride, chloride, bromide and/or iodide. Chlorides are preferable due to the simplicity of using thereof and availability.

As the halide source it is preferable to use a halogen-containing compound of general formula $R_mX_n$, wherein R is an organic or inorganic moiety, X is fluorine, chlorine, bromine or iodine, n>0, and m+n>0.

If R is an inorganic moiety, the moiety is preferably selected from the group consisting of: aluminum, silicon, germanium, boron, lithium, tin, gallium, indium, lead and a mixture thereof.

If R is an organic moiety, it has from 1 to 70 carbon atoms, preferably from 1 to 20 carbon atoms. Preferably, R is a hydrocarbon moiety.

Examples of the halide source can include, but are not limited to: diethylaluminum chloride, butylbromide, aluminum chloride, carbon tetrachloride, boron trichloride, germanium tetrachloride, as well as chloroform ($CHCl_3$), dichloromethane, hexachloroethane, and others halogen-containing compounds.

In addition, the chromium source, alkylaluminum, and/or unsaturated hydrocarbon (mentioned below) can be, at the same time, the halide source for the reaction mixture. The most preferable halide source is alkylaluminum halide that is used together with an alkylaluminum compound, due to the simplicity of using thereof and compatibility. Examples of alkylaluminum halides include, but are not limited to: diethylaluminum chloride ($AlEt_2Cl$), ethylaluminum dichloride ($AlEtCl_2$), dibutylaluminum chloride, diethylaluminum bromide, diethylaluminum iodide and mixtures thereof.

The addition of the halide source to the catalyst system can improve the selectivity, activity and/or productivity thereof.

It is preferable to add the halide source to the trimerization catalyst system when preparing thereof. In particular, it is preferable to use a halogen-containing compound to improve hexene-1 selectivity of the trimerization catalyst systems.

Preferably the components of the catalyst systems are mixed in the presence of a common solvent. Among solvents, hydrocarbon solvents are preferable. Stable and active trimerization and/or oligomerization catalyst systems comprising chromium can be prepared, for example, in the presence of unsaturated hydrocarbon as described in patent RU 2104088. The use of such hydrocarbon often leads to increasing activity of the resultant catalyst system. Any unsaturated hydrocarbon that has no a negative effect on the formation of the catalyst system can be used. Examples of unsaturated hydrocarbon include, but are not limited to: toluene, xylene, hexene-1, cyclohexene. Said unsaturated hydrocarbon can serve as a common solvent for the components of the catalyst system.

The components of the trimerization and oligomerization catalyst system can be used in any amounts that are sufficient to cause the trimerization reaction when mixing the catalyst system with olefins. In general, to produce the trimerization catalyst system, the following amounts of the components can be mixed: 1 mol of chromium (calculated on the basis of elemental chromium), from 1 to 50 mol of the nitrogene-containing ligand, and from 1 to 300 mol, preferably from 1 to 100 mol, of alkylaluminum (calculated on the basis of elemental aluminum), preferably in an excess of unsaturated hydrocarbon. In case of using the halide source, it is usually taken in an amount from 1 to 150 mol, preferably from 1 to 100 mol, calculated on the basis of an elemental halogen.

Preferably the following ratio of the components is used: 1 mol of chromium (calculated on the basis of elemental chromium): 2-8 mol, preferably 2-4 mol, of the nitrogen-containing ligand: 10-30 mol, preferably 1-20 mol, of aluminum (calculated on the basis of elemental aluminum). In case of the presence of the halogen source, its amount is preferably from 1 to 8 mol of halide (calculated on the basis of elemental halogen).

An excess of the nitrogen-containing ligand, as known from the prior art, does not improve activity, productivity and/or selectivity of the catalyst system. Too much amount of alkylaluminum may reduce activity and/or product selectivity of the prepared system. Too small amount of alkylaluminum may cause incomplete formation of the catalyst system, which, in turn, leads to low activity of the catalyst system and/or to polymer by-product formation. An excess of the optional halide source also can worsen the activity of the catalyst system. In an embodiment of the invention comprising a step of UHF irradiation of the halide source together with alkylaluminum and/or as a part of the catalyst system during its formation, an improved activity and selectivity of the catalyst system as a result of adding the halide source, as well as decreased activity thereof due to an excess of halide, may be caused by a smaller amount of halide when comparing with the catalyst system prepared by the methods without UHF irradiation known in the prior art. As a result, an optimal composition of the system comprises a smaller amount of the reagent. Thus, the reagent consumption decreases, and the efficiency of the process increases.

The reagents can be mixed in any order. Alkylaluminum and the halide source, if used, are preferably added to the mixture of the chromium source and the nitrogen-containing ligand in an unsaturated hydrocarbon solvent.

The components of the catalyst system can be mixed by any conventional prior art method.

A special feature of the present invention is that when preparing the catalyst system, separate components of the mixture are exposed to UHF radiation, also referred to as a microwave radiation, to be activated. UHF frequencies causing the effects described in the present invention may be different. A radiation frequency between 0.2 and 20 GHz is preferable. A radiation frequency of about 2.45 GHz that does not cause radio-frequency interference is most preferable and is widely used in household and industrial UHF radiation sources.

In general, alkylaluminum is activated by UHF radiation. The halide source, if used, also can be exposed to UHF radiation. These compounds can be exposed to UHF radiation before and/or after mixing thereof with the other components of the catalyst system.

Preferably, alkylaluminum and optionally halide, optionally as a solution in a hydrocarbon solvent, are exposed to UHF radiation and then mixed with the chromium source and the nitrogen-containing ligand. During radiation, the irradiated compound or a mixture of compounds are required to be placed into a vessel transparent for UHF radiation, for example glass, fluoroplastic, or polypropylene vessel. Any radiation power and time of irradiation can be used. However, to achieve the best results, it is recommended to use the time of irradiation from 20 sec to 20 min, and the rated UHF radiation power from 100 W to 50,000 W per 1 g of used alkylaluminum (calculated on the basis of elemental aluminum). In general, such irradiation causes heating of alkylaluminum or a solution thereof not more than 10° C. Irradiation for more than 20 minutes usually does not further improve the properties of the prepared catalyst system. Irradiation for less than 20 seconds may be insufficient to significantly change the properties of alkylaluminum and, optionally, halide, which, in turn, causes insufficient increase in the activity and/or selectivity of the prepared catalyst system.

A time period between termination of the irradiation and the beginning of mixing alkylaluminum and optionally halide with the chromium source and the nitrogen-containing ligand can be of any duration; however, it is preferable to minimize such period. It is preferable to begin the mixing step in less than 5 minutes after termination of UHF irradiation to provide the participation of the UHF irradiated alkylaluminum in the formation of the catalyst system since the special features of alkylaluminum obtained in the course of UHF irradiation and influencing on the properties of the formed catalyst system tend to decrease over time down to complete disappearance. Therefore, said time period is desired to be less than 1 minute. If the time period is more than 3 minutes, the properties of the prepared catalyst system can become worsen compared to the system prepared with UHF-irradiated alkylaluminum that has been added in less than one minute after termination of the irradiation. In particular, the activity of the prepared catalyst system can decrease. If the time period between termination of the irradiation and the start of mixing is more than 20 minutes, in practice, there is no difference what alkylaluminum, UHF-irradiated or non-irradiated, will be used for preparing the catalyst system. Alternatively, alkylaluminum and optionally halide can be delivered stepwise for mixing from the UHF radiation-exposed vessel; therefore, the time period for mixing can be any convenient time as long as alkylaluminum does not lose the properties acquired during the UHF radiation.

In another embodiment, alkylaluminum can be exposed to UHF radiation after mixing with the chromium source and the nitrogen-containing ligand. At the same time, alkylaluminum can be also irradiated before mixing with the chromium source and the nitrogen-containing ligand.

All operations of preparing the trimerization catalyst system are desired to be performed under conditions excluding any contact of the components of the catalyst system with water and air oxygen. The contact of alkylaluminum and the trimerization catalyst system with moisture and oxygen after mixing all the components of the system, including alkylaluminum, is especially recommended to be avoided.

The reaction can occur at any temperature. the temperature at which the reaction mixture is liquid is preferred temperature for providing the reaction to occur. Pressure of the reaction can be any pressure provided that it does not influence on the reaction negatively. The pressure of from atmospheric pressure to 3 atmospheres is usually acceptable. It is convenient to carry out the reaction under the atmospheric pressure.

Reaction time may be of any value sufficient for the reaction to be terminated. The reaction time may vary depending on the used reagents, temperature, pressure, and other parameters of the reaction. In general, the reaction is terminated in less than a day. Under preferable conditions, reaction time usually is of from 1 second to 15 minutes. Longer reaction time does not provide further advantages.

After termination of the reaction and formation of the catalyst mixture, it is preferable to remove an unsaturated hydrocarbon solvent from the mixture. As it is known from RU 2104088 patent, the presence of unsaturated aromatic hydrocarbon in the reaction mixture during oligomerization and/or trimerization can reduce activity of the catalyst system and increase the amount of by-products, such as polymers. The solvent can be removed by any known method, for example by generating a negative pressure (evacuation).

The prepared catalyst system can be added to the trimerization and/or oligomerization reaction by any known technical method in diluted or undiluted form. In case of dilution, it is preferable to use a hydrocarbon solvent. For the above reasons, it is especially preferable to use for dilution of a saturated hydrocarbon solvent or a mixture thereof.

The trimerization and/or oligomerization reaction, wherein there are used the catalysts prepared according to the present invention, can be performed according to any chromium-based trimerization method known in the prior art. Olefins with one double bond at the position 1, having from 2 to 30 carbon atoms/molecule, and without branching at position 2 and, preferably, at position 3, can be used as initial compounds. Examples of such compounds can include, but are not limited to: ethylene, propylene, 1-butene, 1-hexene, 4-methylpentene-1 and mixtures thereof.

The trimerization/co-trimerization process used in the present invention is defined as a combination of the above indicated olefins so that three identical or different molecules, wherein each of the molecules comprises one double bond, were linked in one molecule, forming a compound with one double bond.

Products of the trimerization reaction can be obtained by using the catalyst system according to the present invention via the reaction performed in a solution, a suspension and/or via a gas phase process by using conventional equipment suitable for these purposes and methods of contacting a catalyst system with initial olefins.

In the trimerization and/or oligomerization reaction, temperature and pressure can be of any values suitable for trimerization and/or oligomerization of initial olefins. Temperature of the reaction is typically within a range of from 50° C. to 200° C., preferably from 60° C. to 150° C. Pressure in the reaction is typically within a range of from atmospheric to 150 atmospheres, preferably from 12 to 50 atmospheres.

Hydrogen that, in some cases, accelerates the reaction and/or increases activity of the catalyst system can be added to the reactor.

Saturated or unsaturated hydrocarbons can be used in the reactor as diluents. It is preferable to use saturated hydrocarbons to avoid the formation of polymer by-products. Examples of such hydrocarbons include, but are not limited to: pentane, isopentane, n-hexane, cyclohexane, n-heptane, n-octane, n-nonane.

Products produced in the (co-)trimerization reaction can be used as raw materials for organic synthesis. In particular, they can be used as monomers and comonomers for producing polyolefins and copolymeric polyolefins.

The polymerization or copolymerization reaction can be performed by any method known in the prior art. The polymerization reaction can be performed in a suspension, a solution, or via a gas-phase process.

Various catalysts known in the prior art, such as titanium-magnesium catalysts, vanadium catalysts, chromium catalysts, zirconium catalysts and the like, which are activated by alkylaluminum compounds and/or haloalkylaluminum compounds, can be used as the catalyst for the polymerization reaction.

The polymerization reaction according to the invention can be carried out after the trimerization reaction with preliminary separation of the produced olefin oligomer or several olefin oligomers from the other components of the reaction mixture of the trimerization reaction, followed by contacting olefin oligomers with the polymerization catalyst.

In another embodiment of the invention, the trimerization reaction and the polymerization reaction can be carried out simultaneously in one reactor. In the latter case, copolymerization of the produced olefin oligomer and initial olefin monomer usually occurs.

It is preferable that the trimerization catalyst contacts with an olefin monomer before the polymerization catalyst does in order to provide the presence of the olefin oligomer with a desirable concentration in the reaction mixture before the polymerization reaction. However, an embodiment of the process is also possible, wherein into the reaction mixture comprising the olefin monomer the olefin oligomer is added before the beginning of the reaction, thereby obtaining the initial concentration of the oligomer, followed by adding the trimerization catalyst and the polymerization catalyst.

In another embodiment of the process, an additional olefin monomer comprising from 2 to 6 carbon atoms, for example ethylene, propylene, or hexene-1, is added before the beginning and/or during the polymerization reaction.

In case of using ethylene as an olefin monomer, hexene-1 is mainly produced according to the present invention as an olefin oligomer. The subsequent copolymerization thereof with ethylene, with or without preliminary separation of hexene-1, leads to producing copolymers of ethylene and hexene-1. According to the present invention, by varying the conditions of trimerization and polymerization reactions, and in particular, by varying the ratio of the components, ethylene copolymers with the different amount of butyl substituents in the polymer chain can be produced. In case of introducing hexene-1 into the polymer chain in an amount of 0.01% to 100% by weight, materials of different physical properties, from plastics of various densities to elastomers, can be produced. low density linear polyethylene (LDLPE) the most valuable material that can be produced that is widely applicable as a material for manufacture of packing and other purposes. In the prior art, copolymers of ethylene and hexene-1 having a density of 0.91 to 0.93 g/cm$^3$ are generally referred to as LDLPE.

EXAMPLES

The present invention is illustrated with a series of examples as described below, wherein the following abbreviations are used:

TEA—triethylaluminum
DEAC—diethylaluminum chloride
Cr(EH)$_3$— chromium (III) 2-ethylhexanoate
2,5-DMP—2,5-dimethylpyrrole
1-C6—hexene-1
C6—a mixture of isomeric hexenes
C8—a mixture of isomeric octenes
C10—a mixture of isomeric decenes
C12+—a mixture of heavy unsaturated hydrocarbons, beginning from dodecene
NC—calculated on the basis of normal conditions (273 K, 101325 Pa)
Comp.—comparative The reactions described in the examples below were performed in a stainless steel autoclave-type reactor having a volume of 0.5 l, equipped with a thermostatic system, a paddle stirrer, a temperature and pressure sensors, a gas and liquid dispenser, and an automated control system, under the conditions excluding the contact of the reagents with moisture and air oxygen. The chromium source (anhydrous Cr(EH)$_3$) was prepared by the method described in U.S. Pat. No. 3,962,182 patent, however, the method of dehydration of aqueous Cr(EH)$_3$ had been changed. Aqueous chromium 2-ethylhexanoate was held for 2 hours at 140° C. under vacuum (6 mbar) followed by adding an equal amount (by weight) of 2-ethylhexane acid and holding the obtained mixture for 2 hours at temperature of 185° C. and pressure of 3 mbar, then 1.5 hours at temperature of 200° C. and pressure of 3 mbar. The MARS5 microwave (CEM corporation) was used for UHF irradiation.

The examples below are intended only for illustration of the present invention and do not intended for limiting thereof.

Comparative Example 1

18.5 mg of $Cr(EH)_3$ and 11.0 mg of DMP were placed in a flask. 7 ml of toluene was added. 1.5 ml of a 144 mg/ml solution of TEA in heptane was taken in a dry box and then added to the flask. The color of the solution became grey-brown in 5 minutes. After 15 minutes, the solvents were evaporated under vacuum at room temperature. The residue was diluted with heptane (4 ml). The resultant solution was used in the test of the catalyst system in the ethylene trimerization reaction.

Heptane (125 g) was placed into the reactor. Ethylene (25.6 l, NC) was dosed under stirring. Then the reactor was heated up to 80° C., and this temperature was maintained during the reaction. The ready catalyst system was added to the reactor under hydrogen pressure. The partial hydrogen pressure in the reactor after the addition was about 1.5 bar. Isopropanol (1 ml) was added to the reactor in 30 minutes after the start of the reaction. Then the reactor was cooled to 20° C., excessive pressure was relieved, and the reactor was opened.

Activity, g/(g Cr·hr): 14,700
Total hexane-1 selectivity: 60.7%
The rest of the results of the analysis of the reaction mixture composition are illustrated in Table 1.

Example 1

18.5 mg of $Cr(EH)_3$ and 11.0 mg of DMP were placed into a flask. 7 ml of toluene was added. Toluene (1 ml) was added to 1.5 ml of a 144 mg/ml solution of TEA in heptane. The obtained solution was exposed to UHF radiation for 2.5 minutes at a rated power of 400 W. After that, the solution of TEA comprising $Cr(EH)_3$ and DMP was added into the flask for 40 seconds after termination of the irradiation. The color of the solution became yellowy-brown in 5 minutes. The solvents were evaporated under vacuum at room temperature in 15 minutes. The residue was diluted with heptane (4 ml). The resultant solution was used in the test of the catalyst system in the ethylene trimerization reaction.

Heptane (128 g) was placed into the reactor. Ethylene (25.6 l; NC) was dosed under stirring. Then the reactor was heated up to 80° C., and this temperature was maintained during the reaction. The ready catalyst system was added to the reactor under hydrogen pressure. After the addition, the partial hydrogen pressure in the reactor was about 2 bar. Isopropanol (1 ml) was added to the reactor in 16 minutes after the start of the reaction. Then the reactor was cooled to 20° C., excessive pressure was relieved, and the reactor was opened.

Activity, g/(g Cr·hr): 26,600
Total hexane-1 selectivity: 62.9%
The rest of the results of the analysis of the reaction mixture composition are illustrated in Table 1.

Comparative Example 2

56.0 mg of $Cr(EH)_3$ and 33.0 mg of DPM was placed into a flask. 5 ml of toluene was added. Then, 1.2 ml of a 144 mg/ml solution of TEA in heptane was added. The solvents were evaporated under vacuum at room temperature in 15 minutes. After that, the residue in the flask was diluted with heptane (4 ml). The obtained solution was used in the test of the catalyst system in the ethylene trimerization reaction.

132 g of heptane and 0.40 ml of the 144 mg/ml solution of TEA in heptane were added in the reactor. Ethylene (25.6 l, NC) was dosed through a flowmeter under stirring. Then, the reactor was heated to 80° C. and this temperature was maintained during the reaction. The ready catalyst system was added to the reactor under the pressure of a hydrogen/argon mixture (1:1). After adding the catalyst, partial hydrogen pressure in the reactor was about 1.5 atmospheres. Isopropanol (1.5 ml) was added to the reactor in 30 minutes under the pressure of the gas mixture. The reactor was cooled to 20° C., excessive pressure was relieved, and the reactor was opened.

Activity, g/(g Cr·hr): 3,600
Total hexane-1 selectivity: 66.3%
The rest of the results of the analysis of the reaction mixture composition are illustrated in Table 1.

Example 2

56.0 mg of $Cr(EH)_3$ and 33.0 mg of DMP were placed in a flask. 5 ml of toluene was added. 1.2 ml of a 144 mg/ml solution of TEA in heptane was mixed with 1 ml of toluene. The obtained solution was exposed to UHF radiation for 3 minutes at a rated power of 400 W. After that, a solution of organoaluminum compounds was added in the flask comprising $Cr(EH)_3$ and DMP for 40 seconds after termination of the irradiation. After mixing, the mixture was exposed to UHF radiation under the same conditions for 10 minutes in the closed flask. The solvents of TEA were evaporated under vacuum at room temperature in 15 minutes after the addition. After that, the residue in the flask was diluted with heptane (4 ml). The resultant solution was used in the test of the catalyst system in the ethylene trimerization reaction.

127 g of heptane and 0.40 ml of the 144 mg/ml solution of TEA in heptane were added in the reactor. Ethylene (25.6 l, NC) was dosed through a flowmeter under stirring. Then, the reactor was heated to 80° C., and this temperature was maintained during the reaction. The ready catalyst system was added in the reactor under pressure of hydrogen. After adding the catalyst, partial hydrogen in the reactor was about 2 atmospheres. Isopropanol (1.5 ml) was added to the reactor in 30 minutes after the start of the reaction. Then, the reactor was cooled to 20° C., excessive pressure was relieved, and the reactor was opened.

Activity, g/(g Cr·hr): 6,500
Total hexane-1 selectivity: 56.5%
The rest of the results of the analysis of the reaction mixture composition are illustrated in Table 1.

Examples 1 and 2 demonstrate that the activity of the catalyst system increases in case of UHF irradiation of alkylaluminum before mixing thereof with a chromium source in comparison with similar examples without using UHF irradiation.

Comparative Example 3

38.0 mg of $Cr(EH)_3$ and 22.0 mg of DMP were placed in a flask. 7 ml of toluene was added. 0.8 ml of a 144 mg/ml solution of TEA in heptane was mixed with 1.1 ml of a solution comprising TEA (32 mg/ml) and DEAC (25 mg/ml) in toluene, and the obtained solution was added to $Cr(EH)_3$ and DMP in toluene. The solvents were evaporated under vacuum at room temperature in 20 minutes. After that, the residue in the flask was diluted with heptane (4 ml). The obtained solution was used in the test of the catalyst system in the ethylene trimerization reaction.

132 g of heptane and 0.5 ml of the 144 mg/ml solution of TEA in heptane were added to the reactor. Ethylene (29.5 l, NC) was dosed through a flowmeter under stirring. Then, the reactor was heated to 80° C., and this temperature was maintained during the reaction. The ready catalyst system was added into the reactor under pressure of argon. Isopropanol (1.5 ml) was added to the reactor in 12 minutes after the start of the reaction. Then the reactor was cooled to 20° C., excessive pressure was relieved, and the reactor was opened.

Activity, g/(g Cr·hr): 12,400
Total hexene-1 selectivity: 72.9%
The rest of the results of the analysis of the reaction mixture composition are illustrated in Table 1.

Example 3

38 mg $Cr(EH)_3$ and 22.0 mg DMP were placed in a flask. 7 ml of toluene was added. 0.8 ml of a 144 mg/ml solution of TEA in heptane was mixed with 1.1 ml of a solution of TEA (32 mg/ml) and DEAC (25 mg/ml) in toluene. The obtained solution was exposed to UHF radiation for 3 minutes at a rated power of 400 W. After that, a solution of organoaluminum compounds was added to the flask comprising $Cr(EH)_3$ and DMP for 40 seconds after termination of the irradiation. The solvents were evaporated under vacuum at room temperature in 20 minutes. Then, the residue in the flask was diluted with heptane (4 ml). The resultant solution was used in the test of the catalyst system in the ethylene trimerization reaction.

132 g of heptane and 0.5 ml of the 144 mg/ml solution of TEA in heptane were added in the reactor. Ethylene (29.5 l, NC) was dosed through a flowmeter under stirring. Then, the reactor was heated to 80° C., and this temperature was maintained during the reaction. The ready catalyst system was added to the reactor under pressure of argon. Isopropanol (1.5 ml) was added to the reactor in 12 minutes after the start of the reaction. Then, the reactor was cooled to 20° C., excessive pressure was relieved, and the reactor was opened.

Activity, g/(g Cr·hr): 28,700
Total hexene-1 selectivity: 85.0%
The rest of the results of the analysis of the reaction mixture composition are illustrated in Table 1.

Example 3 and a comparative example 3 demonstrate that both the activity and the target product selectivity of the catalyst systems increase in case of UHF irradiation of alkylaluminum and a halide source in comparison with similar examples without UHF radiation.

Comparative Example 4

38.0 mg of $Cr(EH)_3$ and 22.0 mg of DMP were placed in a flask. 5 ml of toluene was added. 0.9 ml of a 154 mg/ml solution of TEA in heptane and 0.6 ml of a 37 mg/ml solution of DEAC in heptane was mixed with 0.5 ml of toluene. The resultant solution was added in the flask comprising $Cr(EH)_3$ and DMP. The solvent was evaporated under vacuum at room temperature in 15 minutes. Then the residue in the flask was diluted with heptane (4 ml). The resultant solution was used in the test of the catalyst system in the ethylene trimerization reaction.

130 g of heptane and 0.5 ml of the 154 mg/ml solution of TEA in heptane were added to the reactor. Ethylene (29.4, NC) was dosed through a flowmeter under stirring. Then, the reactor was heated to 80° C., and this temperature was maintained during the reaction. The ready catalyst system was added in the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 4,500
Total hexene-1 selectivity: 85.7%
The rest of the results of the analysis of the reaction mixture composition are illustrated in Table 1.

Example 4

38.0 mg of $Cr(EH)_3$ and 22.0 mg of DMP were placed in a flask. 5 ml of toluene was added. 0.9 ml of a 154 mg/ml solution of TEA in heptane and 0.6 ml of a 37 mg/ml solution of DEAC in heptane were mixed with 0.5 ml of toluene. The obtained solution was exposed to UHF radiation for 1 minute at a rated power of 400 W. After that, a solution of organoaluminum compounds to $Cr(EH)_3$ and DMP in toluene was added for 40 seconds after termination of the irradiation. The solvent was evaporated under vacuum at room temperature in 15 minutes. Then, the residue in the flask was diluted with heptane (4 ml). The resultant solution was used in the test of the catalyst system in the ethylene trimerization reaction.

133 g of heptane and 0.5 ml of the 154 mg/ml solution of TEA in heptane were added to the reactor. Ethylene (29.4 l, NC) was dosed through a flowmeter under stirring. Then, the reactor was heated to 80° C., and this temperature was maintained during the reaction. The ready catalyst system was added to the reactor under pressure of argon. Isopropanol (2 ml) was added to the reactor in 16 minutes after the start of the reaction. Then, the reactor was cooled to 20° C., excessive pressure was relieved, and the reactor was opened.

Activity, g/(g Cr·hr): 9,300
Total hexene-1 selectivity: 70.6%
The rest of the results of the analysis of the reaction mixture composition are illustrated in Table 1.

Example 5

38.0 mg of $Cr(EH)_3$ and 22.0 mg of DMP were placed in a flask. 5 ml of toluene was added. 0.9 ml of a 154 mg/ml solution of TEA in heptane and 0.6 ml of a 37 mg/ml solution of DEAC in heptane were mixed with 0.5 ml of toluene. The obtained solution was exposed to UHF radiation for 6 minutes at a rated power of 400 W. After that, a solution of organoaluminum compounds was added to $Cr(EH)_3$ and DMP in toluene for 40 seconds after termination of the irradiation. The solvent was evaporated under vacuum at room temperature in 15 minutes. Then, the residue in the flask was diluted with heptane (4 ml). The resultant solution was used in the test of the catalyst system in the ethylene trimerization reaction.

131 g of heptane and 0.5 ml of the 154 mg/ml solution of TEA in heptane were added to the reactor. Ethylene (29.4 l, NC) was dosed through a flowmeter under stirring. Then, the reactor was heated to 80° C., and this temperature was maintained during the reaction. The ready catalyst system was added to the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 18,700
Total hexene-1 selectivity: 73.6%
The rest of the results of the analysis of the reaction mixture composition are illustrated in Table 1.

Examples 4 and 5 demonstrate that the activity of the catalyst system increases due to UHF irradiation of alkylaluminum and a halide source in comparison with the test without irradiation (comparative example 4). With that, longer time of irradiation in example 5 results in greater increase in the activity.

Example 6

38.0 mg of Cr(EH)$_3$ and 22.0 mg of DMP were placed in a flask. 5 ml of toluene was added.

0.9 ml of a 154 mg/ml solution of TEA in heptane and 0.6 ml of a 37 mg/ml solution of DEAC in heptane were mixed with 0.5 ml of toluene. The obtained solution of organ.c.oaluminum compounds was added to Cr(EH)$_3$ and DMP in toluene. After 45 seconds, the resultant mixture was exposed to UHF radiation for 6 minutes at a rated power of 400 W. The solvent was evaporated under vacuum at room temperature in 9 minutes after termination of the UHF irradiation. Then the residue in the flask was diluted with heptane (4 ml). The resultant solution was used in the test of the catalyst system in the ethylene trimerization reaction.

142 g of heptane and 0.5 ml of the 154 mg/ml solution of TEA in heptane were added to the reactor. Ethylene (29.4 l, NC) was dosed through a flowmeter under stirring. Then, the reactor was heated to 80° C. and this temperature was maintained during the reaction. The ready catalyst system was added to the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 9,000
Total hexene-1 selectivity: 70.0%

The rest of the results of the analysis of the reaction mixture composition are illustrated in Table 1.

Example 6 demonstrates that UHF irradiation of alkylaluminum comprised in the catalyst system causes the increase in the activity of the system in comparison with the system without UHF irradiation (comparative example 4), but the observed increase was lower than in a case of UHF irradiation of alkylaluminum, during the same period of time, before mixing thereof with a chromium source (example 5).

Example 7

38.0 mg of Cr(EH)$_3$ and 22.0 mg of DMP were placed in a flask. 5 ml of toluene was added. 0.9 ml of a 154 mg/ml solution of TEA in heptane and 0.6 ml of a 37 mg/ml solution of DEAC in heptane were mixed with 0.5 ml of toluene. The obtained solution was exposed to UHF radiation for 6 minutes at a rated power of 400 W. The solution was used for producing a catalyst system by mixing thereof with Cr(EH)$_3$ and DMP in toluene in 3 minutes after termination of the irradiation. The solvent was evaporated under vacuum at room temperature in 15 minutes. Then, the residue in the flask was diluted with heptane (4 ml). The resultant solution was used in the test of the catalyst system in the ethylene trimerization reaction.

137 g of heptane and 0.5 ml of the 154 mg/ml solution of TEA in heptane were added to the reactor. Ethylene (29.4 l, NC) was dosed through a flowmeter under stirring. Then, the reactor was heated to 80° C. and this temperature was maintained during the reaction. The ready catalyst system was added to the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 11,200
Total hexene-1 selectivity: 75.6%

The rest of the results of the analysis of the reaction mixture composition are illustrated in Table 1.

Example 7 compared with example 5 demonstrates that the effect of increase in the activity due to UHF irradiation of alkylaluminum compounds decreases with the prolongation of time between termination of the irradiation and mixing with a chromium source.

Comparative Example 5

76.0 mg of Cr(EH)$_3$ and 44.0 mg of DMP were placed in a flask. 5 ml of toluene was added. Then, 0.85 ml of 154 mg/ml solution of TEA in heptane and 0.3 ml of a 198 mg/ml solution of DEAC in heptane were added. The solvent was evaporated under vacuum at room temperature in 10 minutes. Then, the residue in the flask was diluted with heptane (4 ml). The resultant solution was used in the test of the catalyst system in the ethylene trimerization reaction.

130 g of heptane and 0.5 ml of the 154 mg/ml solution of TEA in heptane were added to the reactor. Ethylene (23.2 l, NC) was dosed through a flowmeter under stirring. Then, the reactor was heated to 80° C. and this temperature was maintained during the reaction. The ready catalyst system was added to the reactor under pressure of argon. The reaction did not in fact occur: the pressure in the reactor was quickly stabilized, the reaction mixture was not heated. Isopropanol (2 ml) was added to the reactor in 16 minutes after the start of the reaction. The reactor was cooled to 20° C., excessive pressure was relieved, and the reactor was opened. Based on the data of the analysis, the reaction mixture comprised a trace amount of hexane-1 and other reaction products, as well as a polymer.

The results are demonstrated in Table 1.

Example 8 mg of Cr(EH)$_3$ and 22.0 mg of DMP were placed in a flask. 7 ml of toluene was added. 0.2 ml of a 144 mg/ml solution of TEA in heptane and 1.1 ml of a solution of TEA (32 mg/ml) and DEAC (25 mg/ml) in toluene was exposed to UHF radiation for 3 minutes at room temperature and a rated power of 400 W. After that, the solution of organoaluminum compounds was added to Cr(EH)$_3$ and DMP in toluene for 40 seconds after termination of the irradiation. The solvents were evaporated under vacuum at room temperature in 15 minutes. Then, the residue in the flask was diluted with heptane (4 ml). The resultant solution was used in the test of the catalyst system in the ethylene trimerization reaction.

130 g of heptane and 0.25 ml of the 144 mg/ml solution of TEA in heptane were added to the reactor. Ethylene (29.5 l, NC) was dosed through a flowmeter under stirring. Then, the reactor was heated to 80° C. and this temperature was maintained during the reaction. The ready catalyst system was added to the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 16,200
Total hexene-1 selectivity: 95.5%

The rest of the results of the analysis of the reaction mixture composition are illustrated in Table 1.

Example 9

57.0 mg of Cr(EH)$_3$ and 33.0 mg of DMP were placed in a flask. 5 ml of toluene was added. 0.7 ml of a 154 mg/ml solution of TEA in heptane and 0.3 ml of a 198 mg/ml solution of DEAC in heptane were mixed with 1 ml of toluene. The resultant solution was exposed to UHF radiation for 3 minutes at a rated power of 400 W. After that, the solution of organoaluminum compounds was added to $Cr(EH)_3$ and DMP in toluene for 40 seconds after termination of the irradiation. The color of the solution became yellow-brown in 15 minutes. The solvent was evaporated at room temperature under vacuum. Then, the residue in the flask was diluted with heptane (4 ml). The resultant solution was used in the test of the catalyst system in the ethylene trimerization reaction.

136 g of heptane and 0.45 ml of the 144 mg/ml solution of TEA in heptane were added to the reactor. Ethylene (29.5 l, NC) was dosed through a flowmeter under stirring. Then, the reactor was heated to 80° C. and this temperature was maintained during the reaction. The ready catalyst system was added to the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 5,800
Total hexene-1 selectivity: 97.4%
The rest of the results of the analysis of the reaction mixture composition are illustrated in Table 1.

Examples 8 and 9 demonstrate the possibility to achieve high selectivity of the reaction in lower amount of organoaluminum compounds, and considerable decrease in amount of formed decenes (C10) by-products. For comparison, in patent RU 2104088, the activity of the catalyst system with the $Cr(EH)_3$:DMP:TEA:DEAC ratio of 1:3:15:3 in the reaction of ethylene oligomerization without UHF irradiation was 16,800 g/(g Cr·hr) at ethylene pressure of 38 bar; the hexane-1 selectivity was 86%. In U.S. Pat. No. 6,455,648, the maximal hexane selectivity was 96.4% in the $Cr(EH)_3$:DMP:TEA:DEAC ratio of 1:3:11:8 and ethylene pressure of 51 bar.

Comparative Example 6

38.0 mg of $Cr(EH)_3$ and 22.0 mg of DMP were placed in a flask. 5 ml of toluene was added. 0.9 ml of a 154 mg/ml solution of TEA in heptane was mixed with 0.4 ml of a 198 mg/ml solution of DEAC in heptane. The resultant solution was added to $Cr(EH)_3$ and DMP in toluene. The solvent was evaporated under vacuum at room temperature in 15 minutes. Then, the residue in the flask was diluted with heptane (4 ml). The resultant solution was used in the test of the catalyst system in the ethylene trimerization reaction.

133 g of heptane and 0.3 ml of the 154 mg/ml solution of TEA in heptane were added to the reactor. Ethylene (29.4 l, NC) was dosed through a flowmeter under stirring. Then, the reactor was heated to 80° C. and this temperature was maintained during the reaction. The ready catalyst system was added to the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 28,800; the average pressure during the reaction: 19.5 bar.
Total hexene-1 selectivity: 94.9%
The rest of the results of the analysis of the reaction mixture composition are illustrated in Table 1.

Example 10

38.0 mg of $Cr(EH)_3$ and 22.0 mg of DMP were placed in a flask. 5 ml of toluene was added. 0.8 ml of a 154 mg/ml solution of TEA in heptane was mixed with 0.2 ml of a 198 mg/ml solution of DEAC in heptane. The obtained solution was exposed to UHF radiation for 6 minutes at a rated power of 400 W. After that, the solution of organoaluminum compounds was added to $Cr(EH)_3$ and DMP in toluene for 40 seconds after termination of the irradiation. The solvent was evaporated under vacuum at room temperature in 15 minutes. Then, the residue in the flask was diluted with heptane (4 ml). The resultant solution was used in the test of the catalyst system in the ethylene trimerization reaction.

129 g of heptane and 0.3 ml of the 154 mg/ml solution of TEA in heptane were added to the reactor. Ethylene (29.4 l, NC) was dosed through a flowmeter under stirring. Then, the reactor was heated to 80° C. and this temperature was maintained during the reaction. The ready catalyst system was added to the reactor under pressure of argon. Isopropanol (2 ml) was added to the reactor in 16 minutes after the start of the reaction. Then the reactor was cooled to 20° C., excessive pressure was relieved, and the reactor was opened.

Activity, g/(g Cr·hr): 53,700; the average pressure during the reaction: 20.4 bar.
Total hexene-1 selectivity: 88.9%
The rest of the results of the analysis of the reaction mixture composition are illustrated in Table 1.

Example 10 demonstrates the possibility to achieve high activity of the catalyst system at lower average pressure of ethylene. For comparison, in patent RU 2104088, the maximal activity of the catalyst system in the ethylene oligomerization reaction was 66,400 g/(g Cr·hr) at the ethylene pressure of 38 bar (example 8012). In U.S. Pat. No. 7,384,886, the activity of the catalyst in the use of a batch reactor was 34,325 g/(g Cr·30 minutes), or 68,650 g/(g Cr·hr), at the ethylene pressure of 46 bar (example 4).

Comparative Example 7

28.5 mg of $Cr(EH)_3$ and 16.5 mg of DMP was placed in a flask. 2.5 ml of heptane was added. 2.2 ml of a 154 mg/ml solution of TEA in heptane was mixed with 0.7 ml of a 20 mg/ml solution $CHCl_3$ in heptane. The resultant solution was added to $Cr(EH)_3$ and DMP in toluene. The resultant solution was used in the test of the catalyst system in the ethylene trimerization reaction in 15 minutes.

132 g of heptane was added to the reactor. Ethylene (25.8 l, NC) was dosed through a flowmeter under stirring. Then, the reactor was heated to 80° C. and this temperature was maintained during the reaction. The ready catalyst system was added to the reactor under pressure of argon. Isopropanol (3 ml) was added to the reactor in 16 minutes after the start of the reaction. Then the reactor was cooled to 20° C., excessive pressure was relieved, and the reactor was opened.

Activity, g/(g Cr·hr): 5,500
Total hexene-1 selectivity: 81.6%
The rest of the results of the analysis of the reaction mixture composition are illustrated in Table 2.

Example 11

28.5 mg of $Cr(EH)_3$ and 16.5 mg of DMP were placed in a flask. 2.5 ml of heptane was added. 2.2 ml of a 154 mg/ml solution of TEA in heptane was exposed to UHF radiation for 6 minutes at a rated power of 400 W. The solution was mixed with 0.7 ml of a 20 mg/ml solution of $CHCl_3$ in heptane. Then, not later than 40 seconds after termination of the irradiation, the resultant mixture was added to $Cr(EH)_3$ and DMP in toluene. The resultant solution was used in the test of the catalyst system in the ethylene trimerization reaction in 15 minutes.

132 g of heptane was added to the reactor. Ethylene (29.4 l, NC) was dosed through a flowmeter under stirring. Then, the reactor was heated to 80° C. and this temperature was maintained during the reaction. The ready catalyst system was added to the reactor under the argon pressure. Ethanol (3 ml) was added to the reactor in 16 minutes after the start of the reaction. Then the reactor was cooled to 20° C., excessive pressure was relieved, and the reactor was opened.

Activity, g/(g Cr·hr): 12,400

Total hexene-1 selectivity: 86.9%

The rest of the results of the analysis of the reaction mixture composition are illustrated in Table 2.

Example 12

28.5 mg of Cr(EH)$_3$ and 16.5 mg of DMP were placed in a flask. 2.5 ml of heptane was added. 2.2 ml of a 154 mg/ml solution of TEA in heptane was mixed with 0.7 ml of a 20 mg/ml solution of CHCl$_3$ in heptane. The resultant solution was exposed to UHF radiation for 6 minutes at a rated power of 400 W. Then, not later than 40 seconds after termination of the irradiation, the resultant mixture was added to Cr(EH)$_3$ and DMP in toluene. The resultant solution was used in the test of the catalyst system in the ethylene trimerization reaction in 15 minutes.

122 g of heptane was added to the reactor. Ethylene (29.4 l, NC) was dosed through a flowmeter under stirring. Then, the reactor was heated to 80° C. and this temperature was maintained during the reaction. The ready catalyst system was added to the reactor under pressure of argon. Ethanol (3 ml) was added to the reactor in 16 minutes after the start of the reaction. Then the reactor was cooled to 20° C., excessive pressure was relieved, and the reactor was opened.

Activity, g/(g Cr·hr): 24,700

Total hexene-1 selectivity: 77.6%

The rest of the results of the analysis of the reaction mixture composition are illustrated in Table 2.

Example 13

111.0 mg of Cr(EH)$_3$ and 66.0 mg of DMP were placed into a 50 ml round-bottom flask. 5 ml of toluene was added. 1.9 ml of a 216 mg/ml solution of TEA in heptane was mixed with 5 ml of a 24.1 mg/ml solution of DEAC in heptane. The resultant solution was exposed to UHF radiation for 6 minutes at a rated power of 400 W. Then, not later than 40 seconds after termination of the irradiation, the resultant mixture was added to Cr(EH)$_3$ and DMP in toluene. The solvent was evaporated under vacuum at room temperature in 15 minutes. Then, the rest in the flask was diluted by heptane (14 ml). The resultant solution was used in the test of the catalyst system in the ethylene trimerization reaction.

406 g of heptane was added to the 2 l reactor. Ethylene (39 l) was dosed through a flowmeter under stirring (800 rpm). The reactor was heated to 80° C. Before the start of the reaction, the pressure in the reactor was 16 bar at 80° C. During the reaction, the pressure was maintained at 16 bar by adding ethylene through a flowmeter, the reaction mixture was stirred at 1000 rpm.

The catalyst system was added batchwise to the reactor at pressure of ethylene. The first batch comprised 3.2 mg of Cr. The next batches comprised 1.6 mg of Cr. The second batch was added to 8 minutes after feeding the first one. The third batch was added to 10 minutes after feeding the second one. The fourth batch was added in 30 minutes after feeding the third one.

Isopropanol (3 ml) was added to the reactor in 128 minutes after the start of the reaction. Then the reactor was cooled to 20° C., excessive pressure was relieved, and the reactor was opened.

Table 3 demonstrates the amount of the products formed during the prescribed time period from the start of the reaction, based on the amount of the absorbed ethylene. Activity is indicated on the basis of the average amount of Cr in the reactor on the prescribed time period. The yield is indicated on the basis of the total amount of Cr in the reactor on the prescribed time period. Table 4 summarized the results of the analysis of the product composition in the reaction after termination of the reaction.

TABLE 1

| example | Cr, mg | Pressure of C$_2$H$_4$ initial | Pressure of C$_2$H$_4$ final | Pressure of C$_2$H$_4$ average | Cr:TEA:DEAC ratio | Liquid products, g | Polymer, g | Polymer/liquid products, % | Reaction products, % from liquid products C4 | 1-C6 | C6 | C8 | C10 | C12+ | 1-C6 in hexanes, % | Activity, g of liquid products/(g Cr × hr) |
|---|---|---|---|---|---|---|---|---|---|---|---|---|---|---|---|---|
| Cmpr 1 | 2.0 | 32.4 | 20.0 | 26.1 | 1:50:0 | 14.7 | 0.26 | 1.8 | 5.3 | 60.7 | 8.6 | 2.7 | 13.8 | 8.9 | 87.6 | 14,700 |
| 1 | 2.0 | 31.0 | 20.0 | 23.5 | 1:50:0 | 13.3 | 0.016 | 0.12 | 2.0 | 62.9 | 11.3 | 2.0 | 14.3 | 7.5 | 84.8 | 26,600 |
| Cmpr 2 | 6.0 | 31.2 | 21.9 | 24.6 | 1:17.5:0 | 10.8 | 0.06 | 0.55 | 1.3 | 66.3 | 11.7 | 2.5 | 13.6 | 4.6 | 85.0 | 3,600 |
| 2 | 6.0 | 31.3 | 16.6 | 22.5 | 1:17.5:0 | 19.5 | 0.04 | 0.21 | 0.9 | 56.5 | 7.7 | 2.3 | 18.2 | 14.4 | 88.0 | 6,500 |
| Cmpr 3 | 4.0 | 34.8 | 26.0 | 30.5 | 1:24:3 | 9.9 | 0.06 | 0.61 | 3.2 | 72.9 | 6.0 | 3.5 | 9.3 | 5.0 | 92.5 | 12,400 |
| 3 | 4.0 | 35.1 | 16.6 | 24.7 | 1:24:3 | 22.9 | 0.06 | 0.26 | 0.4 | 85.0 | 3.5 | 1.5 | 6.5 | 3.1 | 96.1 | 28,700 |
| Cmpr 4 | 4.0 | 34.6 | 29.1 | 31.3 | 1:24:2.3 | 4.8 | 0.015 | 0.31 | 0.3 | 85.7 | 3.1 | 4.6 | 5.5 | 0.8 | 96.5 | 4,500 |
| 4 | 4.0 | 34.8 | 26.6 | 29.9 | 1:24:2.3 | 10.0 | 0.016 | 0.16 | 7.3 | 70.6 | 4.8 | 5.3 | 8.3 | 3.6 | 93.6 | 9,300 |
| 5 | 4.0 | 34.9 | 19.3 | 26.4 | 1:24:2.3 | 20.0 | 0.017 | 0.09 | 1.9 | 73.6 | 4.4 | 3.3 | 8.9 | 8.0 | 94.4 | 18,700 |
| 6 | 4.0 | 34.1 | 25.0 | 28.3 | 1:24:2.3 | 9.6 | 0.01 | 0.10 | 5.5 | 70.0 | 6.1 | 5.8 | 10.9 | 1.7 | 92.0 | 9,000 |
| 7 | 4.0 | 32.9 | 22.3 | 26.6 | 1:24:2.3 | 12.0 | 0.025 | 0.21 | 1.8 | 75.6 | 5.2 | 2.7 | 9.9 | 4.9 | 93.6 | 11,200 |
| Cmpr 5 | 4.0 | — | — | — | 1:12:3.2 | <0.1 | 0.3 | — | — | — | — | — | — | — | — | <100 |
| 8 | 4.0 | 35.1 | 21.7 | 27.6 | 1:11.2:3.2 | 17.3 | 0.12 | 0.69 | 0.0 | 95.5 | 0.6 | 1.6 | 1.9 | 0.4 | 99.4 | 16,200 |
| 9 | 6.0 | 33.5 | 24.5 | 29.0 | 1:13:4 | 9.3 | 0.02 | 0.22 | 0.0 | 97.4 | 0.4 | 1.0 | 0.9 | 0.4 | 99.6 | 5,800 |
| Cmpr 6 | 4.0 | 33.0 | 8.1 | 19.2 | 1:20.3:8 | 30.8 | 0.015 | 0.05 | 0.0 | 94.9 | 0.2 | 1.0 | 3.3 | 0.7 | 99.8 | 28400 |
| 10 | 4.0 | 33.8 | 9.0 | 20.5 | 1:18.8:4 | 32.2 | 0.01 | 0.03 | 0.2 | 88.9 | 1.7 | 1.0 | 6.2 | 1.9 | 98.1 | 53700 |

TABLE 2

| Cr, example | mg | Pressure of C$_2$H$_4$ | | | Cr:TEA:CHCl$_3$ ratio | Liquid products, g | Polymer, g | Polymer/ liquid products, % | Reaction products, % from liquid products | | | | | | 1-C6 in hexanes, % | Activity, g of liquid products/ (g Cr × hr) |
|---|---|---|---|---|---|---|---|---|---|---|---|---|---|---|---|---|
| | | initial | final | average | | | | | C4 | 1-C6 | C6 | C8 | C10 | C12+ | | |
| Cmpr 7 | 3.0 | 29.5 | 24.3 | 25.6 | 1:50:2 | 4.4 | 0.037 | 0.9 | 2.1 | 81.6 | 3.4 | 4.8 | 5.2 | 2.9 | 96.0 | 5,500 |
| 11 | 3.0 | 34.1 | 25.4 | 26.7 | 1:50:2 | 9.9 | 0.128 | 1.28 | 1.7 | 86.9 | 3.5 | 2.3 | 4.5 | 1.1 | 96.1 | 12,400 |
| 12 | 3.0 | 32.3 | 14.0 | 19.7 | 1:50:2 | 19.8 | 0.033 | 0.17 | 0.6 | 77.6 | 8.6 | 2.1 | 5.3 | 5.8 | 90.0 | 24,700 |

TABLE 3

| | Time, min | | | | | | |
|---|---|---|---|---|---|---|---|
| | 0 | 15 | 30 | 60 | 90 | 120 | 128 |
| Cr in the reactor, mg | 0 | 4.8 | 6.4 | 8.0 | 8.0 | 8.0 | 8.0 |
| Average Cr amount, mg | 0.0 | 4.0 | 5.0 | 6.0 | 6.7 | 7.0 | 7.1 |
| Olefins, g | 0 | 36.2 | 86.4 | 170.1 | 256.7 | 300.4 | 307.9 |
| Activity, kg/(g Cr × hr) | 0 | 36.7 | 34.5 | 28.2 | 25.6 | 21.4 | 20.4 |
| Yield, kg/g Cr | 0 | 7.5 | 13.5 | 21.3 | 32.1 | 37.6 | 38.5 |

TABLE 4

| Cr, example | mg | Pressure, bar | Cr:TEA:DEAC ratio | Liquid products, g | Polymer, g | Polymer/ liquid products, % | Reaction products, % from liquid products | | | | | | 1-C6 in hexanes, % |
|---|---|---|---|---|---|---|---|---|---|---|---|---|---|
| | | | | | | | C4 | 1-C6 | C6 | C8 | C10 | C12+ | |
| 13 | 8.0 | 16.0 | 1:15.6:4.4 | 307.9 | 0.15 | 0.05 | 0.0 | 86.0 | 0.5 | 0.8 | 10.8 | 1.9 | 99.4 | resultant polymer was filtered and dried under vacuum. The yield of the polymer was 41 g.

In the infrared-spectrum of the resultant polymer, a spectral band was observed at 1377 cm$^{-1}$, which indicated the presence of alkyl substituents in the polymer chain.

The example demonstrates that, by using the trimerization catalyst systems prepared by the advanced method, hexane-1 can be produced from ethylene at low pressure of ethylene, and the obtained hexane-1 can be copolymerized with ethylene at the same reactor.

Example 14

13.9 mg of Cr(EH)$_3$ and 13.8 mg of DMP were placed into a 50 ml round-bottom flask. 5 ml of toluene was added. 0.58 ml of a 216 mg/ml solution of TEA in heptane was mixed with 0.35 ml of a 120 mg/ml solution of DEAC in heptane. The resultant solution was exposed to UHF radiation for 6 minutes at a rated power of 400 W. Then, not later than 30 seconds after termination of the irradiation, the resultant mixture was added to Cr(EH)$_3$ and DMP in toluene. The solvent was evaporated under vacuum at room temperature in 15 minutes. To prepare a catalyst, the residue in the flask was diluted with 14 ml of heptane.

700 ml of n-heptane was added to the 2 l reactor. Ethylene (20.0 l) was dosed through a flowmeter under stirring (800 rpm). The reactor was heated to 80° C. and the prepared solution of the catalyst in heptane was added thereto. During the reaction, the temperature was maintained at 80° C. and pressure was maintained at 8 bar by adding ethylene through a flowmeter; the reaction mixture was stirred at 1000 rpm.

In 1 hour, The amount of ethylene absorption was 55.6 g, the activity of the trimerization catalyst was 37 kg/(g Cr·hr), or 1,427 g/(g Al hr). The concentration of hexane-1 in the sample from the reactor was 9.5%.

Then, the pressure in the reactor was reduced down to 4 bar, 1 l of hydrogen and 1.5 ml of the 216 mg/ml solution of TEA in heptane. The reactor was cooled to 65° C. and 29 mg of a suspension of a titanium-magnesium catalyst TS-115 in 4 ml of n-heptane was added thereto. During the reaction, the temperature was maintained at 65° C. The pressure in the reactor was reduced to atmospheric pressure in 30 minutes and the reaction mixture was discharged from the reactor. The Example 15

111.0 mg of Cr(EH)$_3$ and 66.0 mg of DMP were placed into a 50 ml round-bottom flask. 5 ml of toluene was added and the flask was filled by dried nitrogen.

1.9 ml of a 216 mg/ml solution of TEA in heptane was mixed with 5.0 ml of a 24.1 mg/ml solution of DEAC in heptane. The resultant solution was exposed to UHF radiation for 6 minutes at a rated power of 400 W. Then, not later than 30 seconds after termination of the irradiation, the resultant mixture was added to Cr(EH)$_3$ and DMP in toluene. The solvent was evaporated under vacuum at room temperature in 15 minutes. To prepare a catalyst, the residue in the flask was diluted with 8 ml of heptane.

750 ml of n-heptane was added to the 2 l reactor. Ethylene (39.7 l) and hydrogen (250 ml) were dosed through flowmeters. The reactor was heated to 80° C. Before the start of the reaction, the pressure in the reactor was 16.4 bar at 80° C. The prepared solution of the catalyst was added to the reactor. During the reaction, the temperature was maintained at 80° C. and pressure was maintained at 8 bar by adding ethylene through a flowmeter; the reaction mixture was stirred at 1000 rpm. In 2 hour after adding the catalyst, the reaction was quenched by adding 1 ml of butanol. The amount of ethylene absorption was 299 g (37 kg/g Cr).

The reaction mixture was fractionated by distillation on a laboratory rectifying column. A fraction with vapor temperature of 64-65.5° C. was gathered from the top of the column. The amount of hexane-1 was 96%, other olefins—0.7%; cyclohexane—3%. The obtained hexane-1 was used as an initial compound for production of polyhexene.

The following two solutions were prepared for prepolymerization: 1) 55 ml of heptane, 4 ml of a 97 mg/ml solution of DEAC in heptane, 7 ml of hexene-1 and 2) 15 ml of heptane, 2 ml of the solution of DEAC, 1.2 ml of a catalyst suspension—microspheric titanium trichloride (0.47 g/l $TiCl_3$). The solutions were mixed. Then, the combined solution was added to 100 ml of previously prepared hexene-1 in a plastic container in 1 hour. The reaction mixture was held for 2 days at room temperature. Then, solid polymer was removed from the container, crushed and dried on air for 5 days. The yield of polyhexene in the form of transient elastic mass was 57 g.

The example demonstrates that ethylene trimer (hexane-1) separated from the reaction mixture can serve as a monomer in a polymerization reaction.

Example 16

9.5 mg of $Cr(EH)_3$ and 28.1 mg of DMP were placed into a 50 ml round-bottom flask. 5 ml of toluene was added; the flask was filled with dried nitrogen.

1.45 ml of a 216 mg/ml solution of TEA in heptane was mixed with 1.0 ml of a 24.1 mg/ml solution DEAC in heptane. The resultant solution was exposed to UHF radiation for 6 minutes at a rated power of 400 W. Then, not later than 30 seconds after the termination of irradiation, the resultant mixture was added to $Cr(EH)_3$ and DMP in toluene. The solvent was evaporated under vacuum at room temperature in 15 minutes. To prepare a catalyst, the residue in the flask was diluted by 8 ml of heptane.

700 ml of cyclohexane was added to the 2 l reactor. The reactor was heated to 80° C. Ethylene was added to the reactor to pressure of 19 bar. The prepared solution of a catalyst was added to the reactor. During the reaction, the temperature was maintained at 80° C. and pressure was maintained at 20 bar by adding ethylene through a flowmeter; the reaction mixture was stirred at 800 rpm. In 30 minutes after adding the catalyst, the pressure in the reactor was reduced to atmospheric pressure and the reactor was cooled to 0° C. The sample from the reactor comprised 13.3% of hexane-1 and 0.5% of a mixture of docenes. The amount of ethylene absorption before reducing the pressure was 88.0 g (88 kg/g Cr). 10 ml of a 24.1 mg/ml solution of DEAC in heptane and 1 ml of a catalyst suspension—microspheric titanium trichloride (0.47 g/l $TiCl_3$) were added. The reaction was quenched by adding 5 ml of isopropanol In 2 hour. The solvent was evaporated and the residue was dried on air for 7 days, then at 10 mbar and 50° C. for 24 hours. The yield of elastic polymer with an average molecular weight of $8.76 \times 10^6$ and dispersion of 7.7 was 42 g.

The example demonstrates that the resultant mixture of ethylene oligomers with the prevalence of hexane-1 can be polymerized in the same reactor.

What is claimed is:

1. A method for preparing a catalyst system which effects the (co-)trimerization of an olefin monomer, the method comprising mixing a chromium source compound, a nitrogen-containing ligand, and an alkylaluminum to provide a catalyst system in solution, wherein the alkylaluminum is exposed to a frequency of UHF radiation selected from a range of 0.2 to 20 GHz.

2. The method according to claim 1, wherein the alkylaluminum is exposed to UHF radiation for from 0.5 to 20 minutes.

3. The method according to claim 1, wherein the frequency of UHF radiation is about 2.45 GHz.

4. The method according to claim 1, wherein the nitrogen-containing ligand comprises a pyrrole ring.

5. The method according to claim 4, wherein the nitrogen-containing ligand is 2,5-dimethylpyrrole.

6. The method according to claim 1, wherein the alkylaluminum is trialkylaluminum.

7. The method according to claim 6, wherein the trialkylaluminum is triethylaluminum.

8. The method according to claim 1, wherein, when preparing the trimerization catalyst, a halide source of formula $R_mX_n$, where R is an organic or inorganic radical, X is fluorine, chlorine, bromine or iodine, n>0, and m+n>0, is further added.

9. The method according to claim 8, wherein R is aluminium, silicon, germanium, hydrogen, boron, lithium, tin, gallium, indium, lead or a mixture thereof.

10. The method according to claim 8, wherein R is a hydrocarbon radical or a metal-organic radical.

11. The method according to claim 8, wherein said halide source is diethylaluminum chloride, ethylaluminum dichloride, or anhydrous aluminum chloride.

12. The method according to claim 1, wherein alkylaluminum is exposed to UHF radiation after mixing thereof with the rest of components of the catalyst mixture.

13. The method according to claim 8, wherein the mixture of alkylaluminum and the halide source is exposed to UHF radiation before mixing thereof with the chromium source and the nitrogen-containing ligand.

14. The method according to claim 8, wherein alkylaluminum is exposed to UHF radiation before mixing thereof with the halide, the chromium source and the nitrogen-containing ligand.

15. The method according to claim 1, wherein the prepared trimerization catalyst system comprises, per 1 mol of chromium source compound calculated on the basis of elemental chromium, 1-50 mol of the nitrogen-containing ligand, 1-300 mol of alkylaluminum calculated on the basis of elemental aluminum, and, when used, 1-150 mol of the halide source calculated on the basis of elemental halogen.

16. The method according to claim 15, wherein the prepared catalyst system comprises, per 1 mol of chromium source compound calculated on the basis of elemental chromium, from 1 mol to 15 mol of the nitrogen-containing ligand, from 5 mol to 100 mol of alkylaluminum calculated on the basis of elemental aluminum, and, when used, from 1 mol to 20 mol of the halide source calculated on the basis of elemental halogen.

17. The method according to claim 1, wherein the method is performed under oxygen- and water-free conditions.

18. The method according to claim 17, wherein the chromium source and the nitrogen-containing ligand are mixed before the addition of alkylaluminum.

19. A catalyst system for the (co-)trimerization and/or (co-)oligomerization of an olefin monomer comprising from 2 to 30 carbon atoms, comprising a chromium source, a nitrogen-containing ligand, an alkylaluminum exposed to a frequency of UHF radiation selected from a range of 0.2 to 20 GHz, and, optionally, a halide source.

20. The catalyst system according to claim 19, wherein the olefin monomer comprises from 2 to 6 carbon atoms.

21. A process of (co-)trimerization and/or (co-)oligomerization of an olefin compound having from 2 to 30 carbon atoms and at least one terminal olefinic double bond, the process comprising a stage of (co-)trimerization and/or (co-)oligomerization in the presence of the catalyst system according to claim 19 or the catalyst system prepared by the method according to claim 1.

22. The process according to claim 21, wherein the olefin compound is ethylene, 1-butene, 1-hexene or a mixture thereof.

23. A process of polymerization or copolymerization of an olefin oligomer produced by the (co-)trimerization and/or (co-)oligomerization process according to claim 21.

24. The process according to claim 23, wherein one or more olefin oligomers formed in the trimerization reaction are separated from the reaction mixture of the trimerization reaction before polymerization.

25. The process according to claim 23, wherein an olefin monomer having from 2 to 6 carbon atoms is added for copolymerization with the olefin oligomer.

26. The process according to claim 25, wherein the olefin monomer is ethylene, propylene, butene-1 or hexene-1.

27. The process according to claim 23, wherein the polymerization or copolymerization of the olefin oligomer is performed simultaneously with the trimerization of the olefin monomer.

28. The method according to claim 1, wherein the mixing includes a reaction mixture which consists essentially of the chromium source compound, the nitrogen-containing ligand, the alkylaluminum and an optional halide source compound.

* * * * *

UNITED STATES PATENT AND TRADEMARK OFFICE
CERTIFICATE OF CORRECTION

PATENT NO. : 8,921,251 B2
APPLICATION NO. : 13/575902
DATED : December 30, 2014
INVENTOR(S) : Timur Mikhailovich Zilbershtein et al.

It is certified that error appears in the above-identified patent and that said Letters Patent is hereby corrected as shown below:

On the title page, under "(73) Assignee," please change the following Assignee information:

"Open Joint Stock Company "Sibur Holding," Moscow (RU)" to
-- Public Joint Stock Company "Sibur Holding," Tyumen Region, Tobolsk, (RU) --

Signed and Sealed this
Twelfth Day of July, 2016

Michelle K. Lee
*Director of the United States Patent and Trademark Office*